United States Patent [19]
Hall, II et al.

[11] Patent Number: 5,635,195
[45] Date of Patent: Jun. 3, 1997

[54] PREMIX FOR ROOM TEMPERATURE STERILANT

[75] Inventors: Robert T. Hall, II, Welch; Bradley K. Onstad, Deephaven, both of Minn.

[73] Assignee: Minntech Corporation, Minneapolis, Minn.

[21] Appl. No.: 559,236

[22] Filed: Nov. 17, 1995

[51] Int. Cl.$^6$ .............................. A01N 9/00; A01N 25/00
[52] U.S. Cl. .............................. 424/405; 422/28
[58] Field of Search .............................. 424/405; 422/28

[56] References Cited

U.S. PATENT DOCUMENTS

| | | | |
|---|---|---|---|
| 5,217,698 | 6/1993 | Siegel et al. | 422/295 |
| 5,545,343 | 8/1996 | Brougham et al. | 514/557 |

FOREIGN PATENT DOCUMENTS

| | | |
|---|---|---|
| 0231632 | 8/1987 | European Pat. Off. . |
| 0269435 | 6/1988 | European Pat. Off. . |
| 387974 | 6/1973 | U.S.S.R. . |

OTHER PUBLICATIONS

D. Kozarov, et al., "Disinfectant Effect of Performic Acid," J. of Hygiene, Epidemiology, Microbiology and Immunology, 19.3, 1975, pp. 389–392 (Czech. Oslovak Medical Press, Prague).

Primary Examiner—Thurman K. Page
Assistant Examiner—Kathryne E. Shelborne
Attorney, Agent, or Firm—Barbara A. Wrigley

[57] ABSTRACT

Provided is an anti-microbial composition containing an ester of formic acid, an oxidizer, performic acid and water. Also provided is a premix for making the anti-microbial composition having two parts. One part contains the ester of formic acid and a second part contains the oxidizer. Another method is provided for making the anti-microbial composition in which the ester of formic acid is combined with the oxidizer and water.

34 Claims, 6 Drawing Sheets

PREMIX FOR ROOM TEMPERATURE STERILANT

BACKGROUND OF THE INVENTION

1. Field of the Invention

The invention relates to a room temperature anti-microbial composition which includes an ester of formic acid, an oxidizer, performic acid, and water, a premix for making the anti-microbial composition, and a method for producing the anti-microbial composition.

2. Background of Related Art

Conventional methods of sterilizing medical devices have significant disadvantages. For example, the steam autoclave works well, but many instruments are sensitive to the high pressure and temperature required to achieve sterility. Ethylene oxide requires long exposure times in a vacuum, even longer aeration times, and the gas is highly toxic. Glutaraldehyde is a suspected carcinogen and can be corrosive to certain materials.

SUMMARY OF THE INVENTION

An object of the present invention is to provide an easy to use room temperature anti-microbial composition.

A further object of the present invention is to provide an anti-microbial composition for sterilizing medical devices which overcomes the disadvantages of known methods of sterilizing medical devices.

The invention relates to an anti-microbial composition having improved anti-corrosive properties comprising an ester of formic acid, an oxidizer, performic acid and water.

A preferred embodiment of the invention relates to an anti-microbial composition having improved anti-corrosive properties comprising about 0.01 to about 10 wt. % of an ester of formic acid selected from the group consisting of ethyl formate, methyl formate, propyl formate, or mixtures thereof, about 0.01 to about 10 wt. % of an oxidizer, about 0.001 to about 5 wt. % of performic acid, and up to about 99.98% water.

The invention also relates to a premix for making the anti-microbial composition comprising two parts. One part comprises the ester of formic acid and a second part comprises the oxidizer.

The invention further relates to a method making the anti-microbial composition comprising the steps of combining the premix.

The invention also relates to a method of producing the anti-microbial composition comprising the steps of combining an ester of formic-acid with an oxidizer and water.

DETAILED DESCRIPTION OF THE PREFERRED EMBODIMENTS

The invention relates to an anti-microbial composition having improved anti-corrosive properties comprising an ester of formic acid, an oxidizer, performic acid and water.

Preferably, the anti-microbial composition comprises about 0.01 to about 10 wt. % of the ester of formic acid, about 0.01 to about 10 wt. % of an oxidizer, about 0.001 to about 5 wt. % of performic acid, and up to about 99.98 wt. % water. More preferably, the anti-microbial composition comprises about 2 to about 8 wt. % of the ester of formic acid, about 1 to 10 wt. % of an oxidizer, about 0.001 to about 1 wt. % of performic acid, and up to about 97 wt. % of water.

Preferably, the ester of formic acid is an ester of ethyl formate, methyl formate, propyl formate, or mixtures thereof. More preferably, the ester of formic acid is ethyl formate.

The oxidizer can be any oxidizer that is compatible with a performic acid based anti-microbial composition. Examples of such oxidizers include nonorganic oxidizing substances such as, hydrogen peroxide, sodium percarbonate, sodium periodate, sodium persulfate, ammonium persulfate, sodium perborate, sodium peroxide, calcium peroxide, silver (II) oxide, ozone, and chlorine dioxide. The oxidizers also include organic oxidizing substances, for example, diacyl peroxides, such as benzoyl peroxide, ketone peroxides, such as 2,4-pentanedione peroxide, peroxydicarbonates, such as diisopropyl peroxydicarbonate, peroxyesters, such as t-butylperoxy maleic acid, dialkyl peroxides, such as dicumyl peroxide, hydroperoxides, such as t-butyl hydroperoxide, and peroxyketals, such as 2,2-di (t-butyl peroxy) butane.

Preferably, the oxidizer is hydrogen peroxide. More preferably, the oxidizer is urea hydrogen peroxide.

A preferred anti-microbial composition comprises ethyl formate in an amount of about 3.8 to about 4 wt. %, urea hydrogen peroxide in an amount of about 1 to about 8 wt. %, and about 0.001 to about 1 wt. % of performic acid.

The anti-microbial composition can also contain additives, such as, corrosion inhibitors and stabilizers.

Examples of corrosion inhibitors are 1,2,3-Benzotriazole, azimidobenzene and benzene azimide (collectively, COBRATEC 99™, PMC Specialties Group, Inc.) and the sodium hydroxide reaction products of an aliphatic alcohol and phosphorous pentoxide (VICTAWET™ 35B, Akzo Chemicals, Inc., Chicago, Ill). The corrosion inhibiting properties of VICTAWET™ 35B are disclosed in PCT/US90/01862, entitled "Anticorrosive Microbicide."

The stabilizers include those that stabilize the anti-microbial composition over time, and those that increase the concentration of performic acid, as well as other stabilizers.

The anti-microbial composition can be made in a concentrated form, dry or liquid, to be diluted with water before using.

Purifying the water is not required. When hard tap water is used, surprisingly, the concentration of performic acid in the anti-microbial composition is less likely to decrease or will increase at the expense of the oxidizer, compared to deionized water. This is a significant advantage, because tap water is more readily available and is less expensive than purified or deionized water. In particular, hard water containing calcium acts in this manner.

The invention also relates to a premix for making the anti-microbial composition comprising a first part comprising an ester of formic acid, and a second part comprising the oxidizer. The oxidizer and ester of formic acid include those described above. The anti-microbial composition can be formed by combining the first and second parts with water.

Preferably, the first part comprises an ester of ethyl formate, methyl formate, propyl formate, or mixtures thereof, and the second part comprises hydrogen peroxide.

Preferably, the amount of the ester of formic acid in the first part and the amount of oxidizer are such that when combined with water the resulting anti-microbial composition comprises about 0.01 to about 10 wt. % of the ester of formic acid, about 0.01 to about 10 wt. % of the oxidizer, about 0.001 to about 5 wt. % of performic acid, and up to about 99.98% water.

Each part of the premix can be in a dry or liquid form. For example, one or both parts of the premix can be diluted with water. Alternatively, one part can contain all of the required water so that when the other part is added no further water is required, or sufficient water is present in both parts so that when both parts are combined no further water is required.

The premix can also contain the above described additives in either or both of the parts.

The invention further relates to a method of making the anti-microbial composition comprising the steps of combining both parts of the pre-mix. If the pre-mix does not contain the required amount of water, water and the first and second parts can be mixed in any order.

Another embodiment of the invention relates to a method of producing the anti-microbial composition comprising the steps of combining the ester of formic acid with the oxidizer and water.

Preferably, sufficient amounts of water, ester of formic acid, and oxidizer are combined so that the resulting anti-microbial composition comprises about 0.01 to about 10 wt. % of the ester of formic acid, about 0.01 to about 10 wt. % of the oxidizer, about 0.001 to about 5 wt. % of performic acid, and up to about 99.98 wt. % water.

The anti-microbial composition can be used in place of conventional microbicides. The following is a partial list of uses for the anti-microbial composition. The uses of the anti-microbial composition is in no way intended to be limited to this list.

The anti-microbial composition can be used on skin, medical devices, and eating utensils.

The anti-microbial composition is particularly useful for reprocessing used catheters which are sensitive to conventional anti-microbial compositions. Preferably, when the anti-microbial composition is used to reprocess used catheters, the anti-microbial composition contains "VICTAWET™ 35b". It is believed that the "Victawet" acts as a lubricant for the mechanical pump during reprocessing. The reprocessing method disclosed in U.S. Pat. Nos. 4,721,123 and 5,310,524 are incorporated herein.

The invention will be further described by the following non-limiting examples.

EXAMPLE 1

Three tests were performed on samples of an anti-microbial composition according to the invention (hereinafter "Perform$_x$") made by combining 3.8 to 4% by weight of ethyl formate, 4% urea hydrogen peroxide, and the balance water. Performic acid was generated in an amount of about 0.001 to about 0.1 wt. %.

The anti-microbial composition was compared to two known microbicides, CIDEX™ 7, a glutaraldehyde based liquid sterilant, (Johnson and Johnson, Medical) and 1% RENALIN® II, a peracetic acid based liquid sterilant (Minntech Corp., published in PCT/US92/05877).

In the first test, the sporicidal and bactericidal activity of each anti-microbial composition was tested by placing ~1×10$^{10}$ *Bacillus subtilis* spores into 10 ml of anti-microbial composition in a closed, but not sealed, test tube at room temperature (about 20° C.). At exposure times of 2.5, 5, 7.5, 10, 12.5, 15, 17.5 and 20 minutes, 1 ml was removed and placed in a neutralizer solution to stop the sterilant action. The neutralizer solution comprised 1% Bacto-peptone (Difco), 1% sodium thiosulfate, and 0.025% catalase. The surviving spores were then serially diluted and plated to count.

Figure 1:
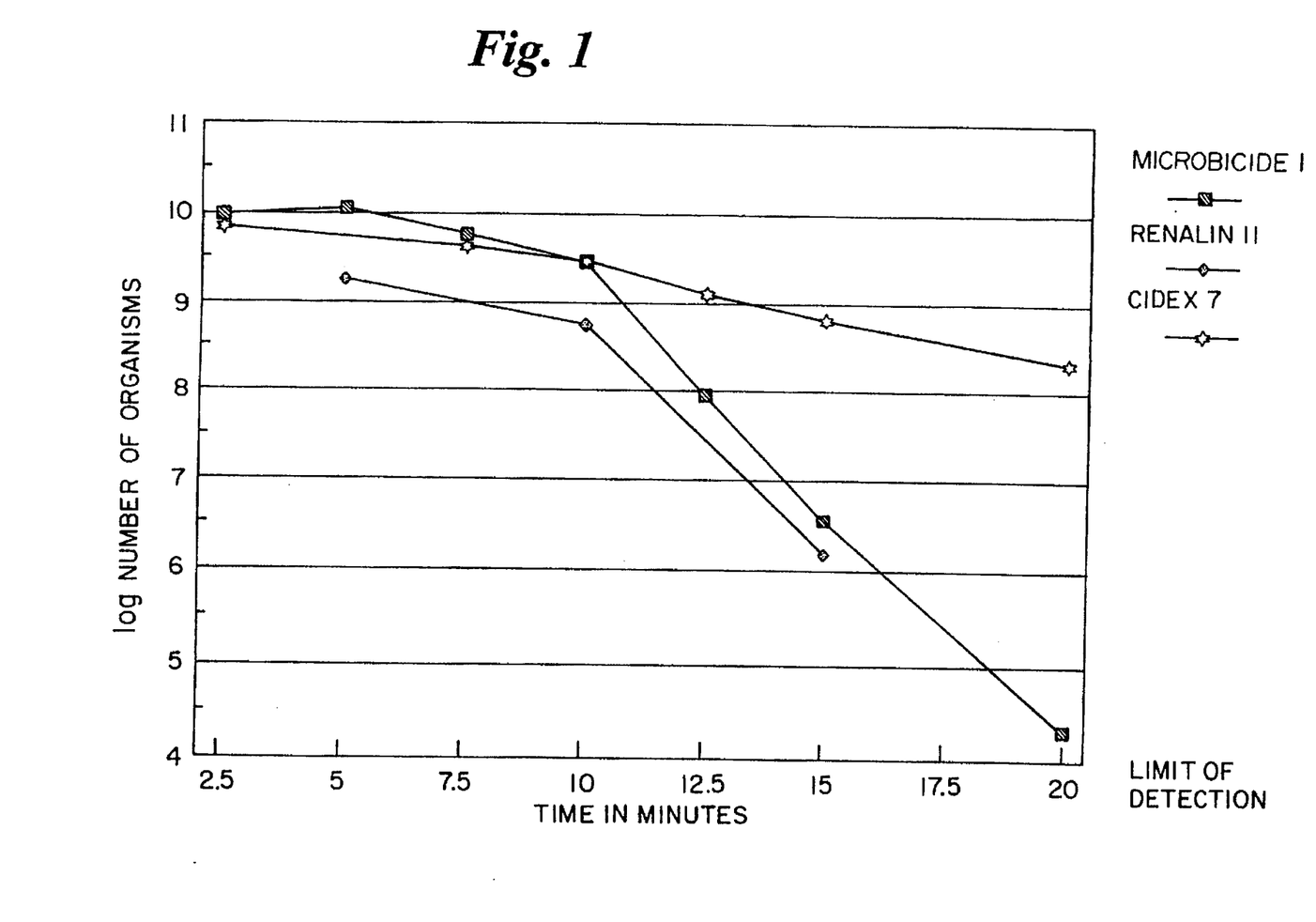
FIG. 1 illustrates the sporicidal effects of the anti-microbial composition according to the invention compared to two conventional anti-microbial compositions.

FIG. 1 illustrates the rate of kill by plotting the log number of surviving organisms vs. exposure time. FIG. 1 illustrates that the Perform$_x$ curve closely fits the 1% RENALIN® II curve. Therefore, Perform$_x$ exhibits anti-microbial effects equal to or greater than 1% RENALIN® II. FIG. 1 also illustrates that Perform$_x$ exhibits significantly greater anti-microbial effects than CIDEX™ 7, on the order of four logs, after 20 minutes.

The above test was repeated, except using methyl formate, butyl formate, or propyl formate in place of ethyl formate in the same molar concentration. After 20 minutes, 5×10$^4$ bacteria were observed and after 60 minutes no bacteria were observed in the methyl formate solution. After 20 minutes, no bacteria were observed and after 60 minutes 6×10$^4$ bacteria were observed in the propyl formate solution. The propyl formate solution was retested and no bacteria was observed after 20 and 60 minutes. Therefore, the bacteria observed after 60 minutes in the propyl formate solution was a procedural error. After 20 minutes, 4.3×10$^7$ bacteria were observed and after 60 minutes 3.3×10$^6$ bacteria Here observed in the butyl formate solution.

Figure 2:
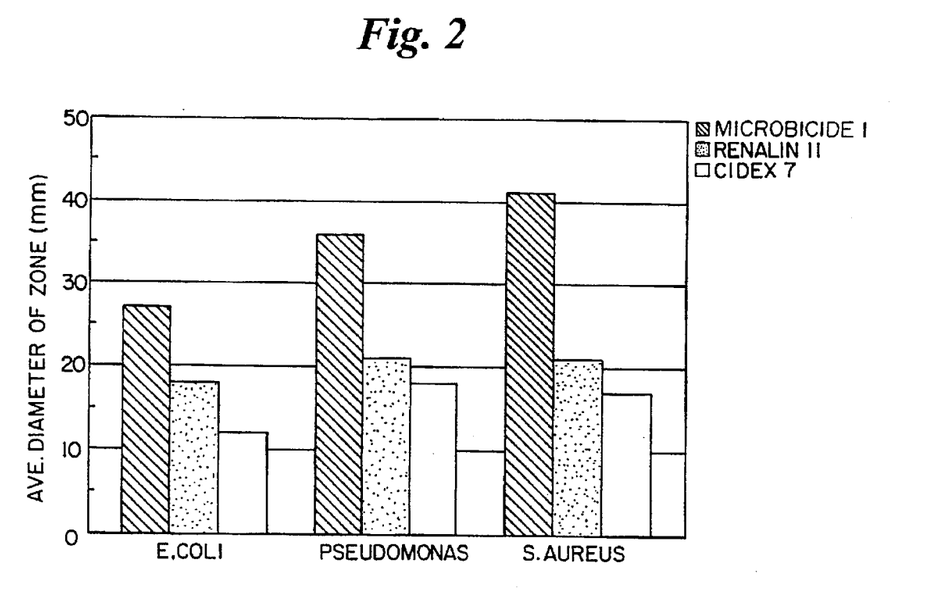
FIG. 2 illustrates the bactericidal effects of the anti-microbial composition according to the invention compared to two conventional anti-microbial compositions.

A second test was performed by coating a petri dish (Falcon Corp.), containing a agar made using tryptic soy (Difco Labs), with either *Staphylococcus aureus*, *Pseudomonas aeruginosa*, or *E. coli*. After the plates were dry, three wells were punched into the agar and filled to the top with either Perform$_x$, Renalin II or CIDEX™ 7. The plates were then incubated for 48 hours at 37° C. The area around the well where no bacteria grew (zone of inhibition) was then measured and graphed. FIG. 2 illustrates the results. The zones where no bacteria grew were significantly larger for the Perform$_x$ than they were for RENALIN® II and CIDEX™ 7. This data illustrates that Perform$_x$ kills significantly more organisms than either of RENALIN® II or CIDEX™ 7, and that Perform$_x$ kills Pseudomonas spp. This is of considerable importance because CIDEX™ 7 has been reported to have difficulty in killing Pseudomonas spp. This test is similar to the test used for determining the relative effectiveness and/or resistance of microorganisms to antibiotics.

A third test was performed in which an AOAC 966.04 (1990) sporicidal test done on *Clostridium spoorogenes* using suture loops as the carrier. The results are summarized in Table 1. All tests were run for 5½ hours at 20° C. unless stated otherwise.

TABLE 1

| Description: | Results (negatives/# samples): |
|---|---|
| Perform$_x$ | 49/50 |
| ½ concentration Perform$_x$ | 19/20 |
| Perform$_x$ pH 7 | 20/20 |
| Perform$_x$ in synthetic hard water | 20/20 |
| Perform$_x$ in tap water | 20/20 |
| Perform$_x$ at 3 ½ hours exposure | 37/40 |
| Perform$_x$ 2 ½ hours exposure | 20/20 |
| Perform$_x$ (double)[1] 12 min. exp. | 19/20 |
| Perform$_x$ (double)[1] 20 min. exp. | 20/20 |
| Perform$_x$ (double)[2] 12 min. exp. | 17/20 |
| Perform$_x$ (double)[2] 20 min. exp. | 20/20 |
| Perform$_x$ (double)[2] 30 min. exp. | 20/20 |

*A tube is considered negative if no growth is observed after 21 days of incubating, heat shocking at 80° C. for 20 minutes and then incubating again for another 72 hours.
[1]Double the amount of urea hydrogen peroxide and ethyl formate, 2 wt. % COBRATEC 99, 50° C.
[2]Double the amount of urea hydrogen peroxide and ethyl formate, 50° C.

A difference of <5 is not statistically significant.

EXAMPLE 2

The corrosive effects of Perform$_x$ were tested using the same formulation of Perform$_x$ as used in Example 1, except where noted.

In the first test, the corrosive effects of Perform$_x$ and 1% RENALIN® II on chrome plated Kerr dental mirrors. The Perform$_x$ formulation tested was the same as in Example 1 except that it did not include COBRATEC 99 and was adjusted to a pH 7 using 0.1N NaOH. The pH of Perform$_x$ before adjusting was 3.8. The mirrors were soaked at room temperature (about 20° C.) in a closed container (screw on lid) for a two week period in about 120 ml of Perform$_x$ or 1% RENALIN® II. The solutions were changed daily by pouring out the used liquid and refilling with fresh.

This test was an appearance type of inspection process rather than a quantitative evaluation. Upon examination after the two week period, the mirrors soaked in Perform$_x$ had a significantly better appearance than the mirrors soaked in 1% RENALIN® II. RENALIN® II etched away the chrome layer, exposing the brass underneath. The brass was beginning to corrode which turned the 1% RENALIN® II solution blue. The Perform$_x$ only slightly dulled the appearance of the chrome plating.

In the second test, the corrosion effects of Perform$_x$ and 3% RENALIN® II on a naval brass coupons (approximately 12.3 gms) were tested. The Perform$_x$ tested was the same as in Example 1 except where noted.

Before testing, the brass coupons were cleaned to remove oils, dirt, etc., by placing the coupons in a glass tray containing acetone and sonicating for about 5 minutes, removing the coupons with forceps, rinsing with deionized water, and then air drying. The coupons were then weighed (Wt1).

The method used to test the corrosion effects is outlined in the ASTM G1-90, (1992) Vol. 3.02, pp. 35–38. Each naval brass coupon was soaked in about 120 ml of test solution for a time period of 24 hours in a plastic specimen cup.

The rate of corrosion was measured using the mass lost during the 24 hour soak period as follows. The naval brass coupons were removed from the test liquids, rinsed thoroughly with deionized water, dried and weighed (Wt2). The corrosion products were then removed from the tested coupons. All of the tested coupons and one blank coupon were submerged in 10% sulfuric acid for 2 minutes while sonicating. The coupons were then rinsed thoroughly with deionized water, air dried and weighed (Wt3). Each coupon was placed on the back of a modified test tube rack in between two glass slides on each side of the coupon. A weighted SCOTCH BRITE™ pad (3M Corp.) was wrapped around each coupon and the coupon was rubbed 10 times each way with the pad, allowing the weight of the pad to be the only downward force exerted on the coupons. Both sides of the coupons were rubbed with the pad. All of the coupons were then placed in 10% sulfuric acid and sonicated for 2 minutes. The coupons were then rinsed, air dried and weighed (Wt4). The coupons were immersed in sulfuric acid and rubbed with the pad as described above until the weight loss of the tested coupons was almost equal to the amount lost by the blank coupon. The weight loss of the tested coupons will not be equal to the amount lost by the blank coupon, but they will usually be within about 0.001 g of each other. Each weight was measured after air drying as (wt$^n$).

The corrosion rate was calculated using the following formula:

$$\text{corrosion rate } (mm/yr) = (K \times W)/(A \times T \times D)$$

where:

A=area of coupon in cm$^2$ to nearest 0.1 cm$^2$(std=28.7 cm$^2$)

K=a constant (8.76×10$^4$)

T=time of exposure in hours to the nearest 0.25 hours.

W=the mass lost in g, to the nearest 1 mg corrected for the mass lost during cleaning (Initial weight$_-$Wt$^n$ of treated coupon) minus (Initial weight–Wt$^n$ of blank coupon).

D=density in g/cm$^3$ of material tested (naval brass c-464- 8.41 g/cm$^3$)

Figure 3:
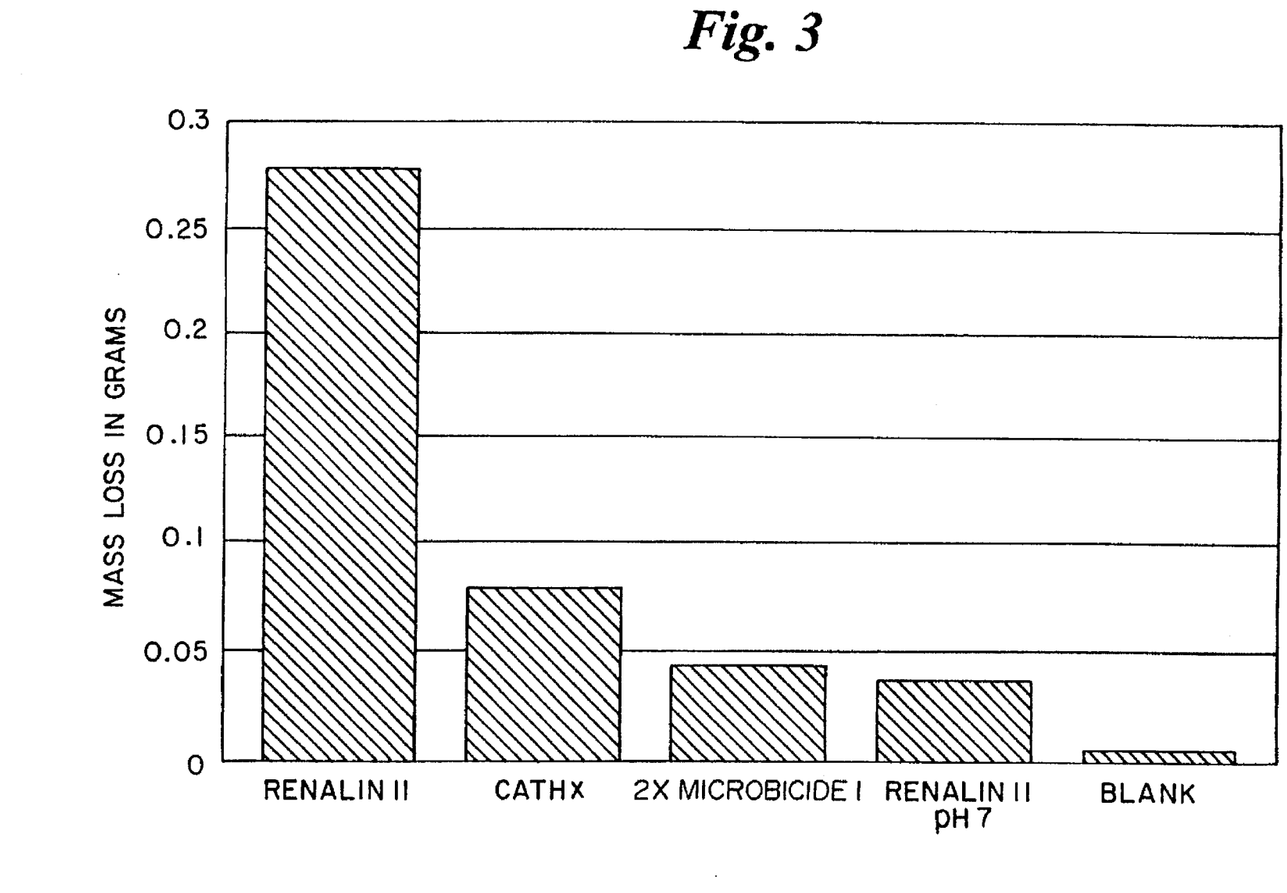
FIG. 3 illustrates the net mass loss of brass after 24 hours of exposure as measured in Example 2.

The results are shown in Table 2 and FIG. 3.

TABLE 2

| SUBSTANCE TESTED: | CORROSION RATE: |
|---|---|
| Perform$_x$ pH 7, 2x concentrate | .57 mm/yr |
| Perform$_x$ pH 7 | 1.40 mm/yr |
| Perform$_x$ pH 7, w/.1% COBRATEC 99 | .061 mm/yr |
| Perform$_x$ w/.1% COBRATEC 99 | .094 mm/yr |
| Perform$_x$ w/.17% COBRATEC 99 | .035 mm/yr |
| Perform$_x$ w/.1% VICTAWET™ 35B | .77 mm/yr |
| Perform$_x$ w/.1% VICTAWET™ 58 | .34 mm/yr |
| Perform$_x$ pH 7, w/.1% sodium nitrite | 1.26 mm/yr |
| Perform$_x$ pH 7.8, w/.1% sodium nitrite | 1.24 mm/yr |
| Cath$_x$ | 1.10 mm/yr |
| 3% RENALIN ® II | 4.13 mm/yr |

The addition of small amounts of COBRATEC 99 significantly reduced the corrosion rate of brass.

In the third test, the corrosion effects of Perform$_x$ and 1% RENALIN® on dental burrs and carbon steel scalpel blades was tested. The Perform$_x$ and 1% RENALIN® II, and the test procedures, were the same as used in the first test of Example 2, except where noted. Perform$_x$ made the burrs tarnish in 24 hours, but the addition of the COBRATEC 99 (0.2%) almost eliminated this problem. To compare, 1% RENALIN® etched the burr away. The scalpel blades showed no signs of corrosion from Perform$_x$, with or without COBRATEC™. 1% RENALIN® performed equally well as Perform$_x$. However, deionized water (deionized using a mixed bed deionizing system) rusted the blades.

EXAMPLE 3

The stability of Perform$_x$ was tested. Formulas 599-81-18 through 599-81-20 used a 1 quart bottle (Twin City Bottle), with vented caps, which was filled with the test solution and the lid screwed on. The 1 quart bottles were stored in a closed cabinet at room temperature (about 20° C.). All of the other formulas used 30 gm glass vials, which were filled with the test solution and the lids screwed on. The vials were stored on an open bench top under fluorescent light at room temperature (about 20° C.). The formulas with a "T" at the end signifies that the test solution was stored at 50° C. instead of 20° C.

The test solution, length of time tested, and the test results are shown in Table 3. The synthetic hard water used was made by the method described in Official Methods of Analysis, Germicidal and Detergent Sanitizing Action of Disinfectants (Final Action) 960.09 page 139 "Synthetic Hard Water" (section E).

Figure 4:
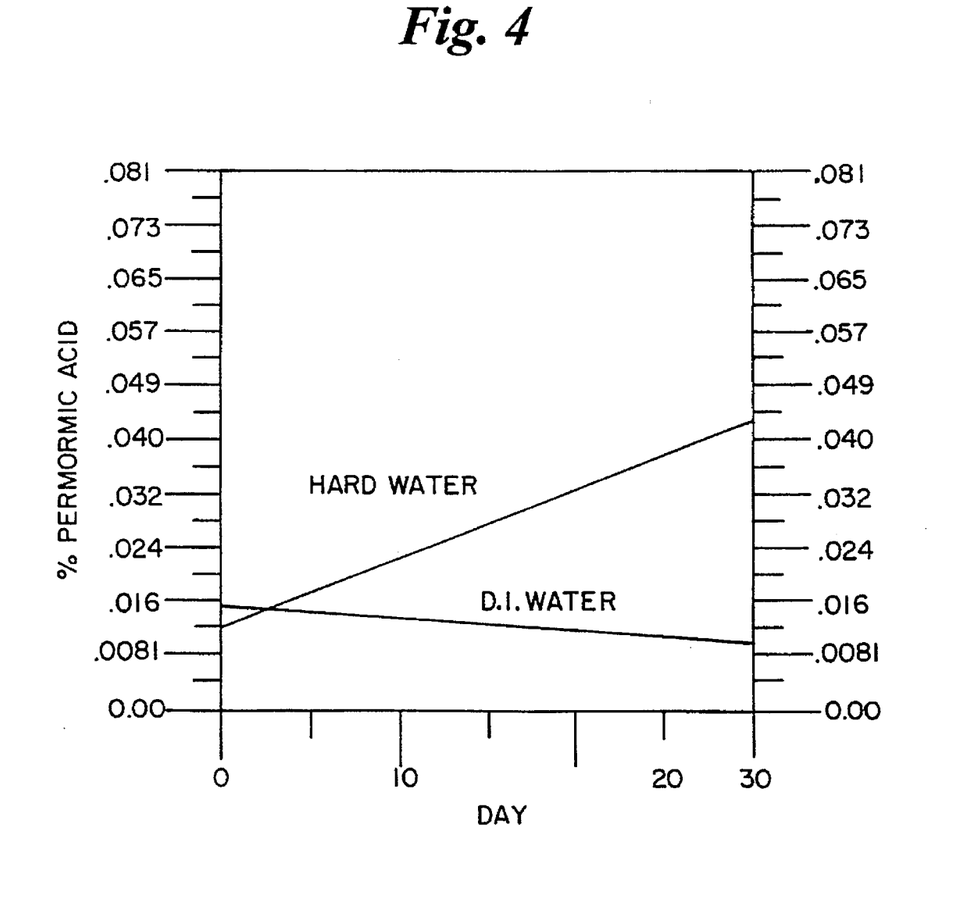
FIG. 4 illustrates the concentration of performic acid in hard and deionized water over time as measured in Example 3.
Figure 5:
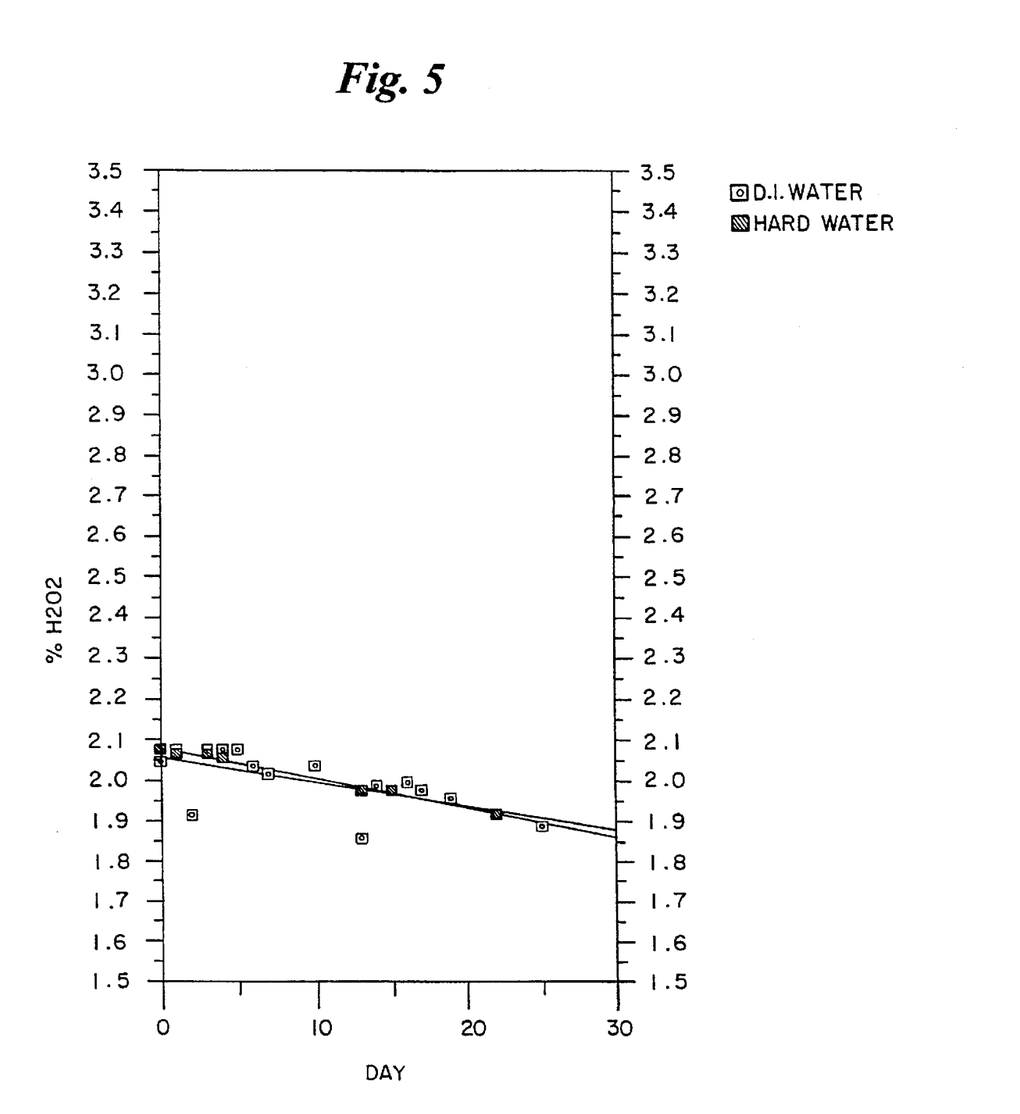
FIG. 5 illustrates the concentration of hydrogen peroxide in hard and deionized water over time as measured in Example 3.
Figure 6:
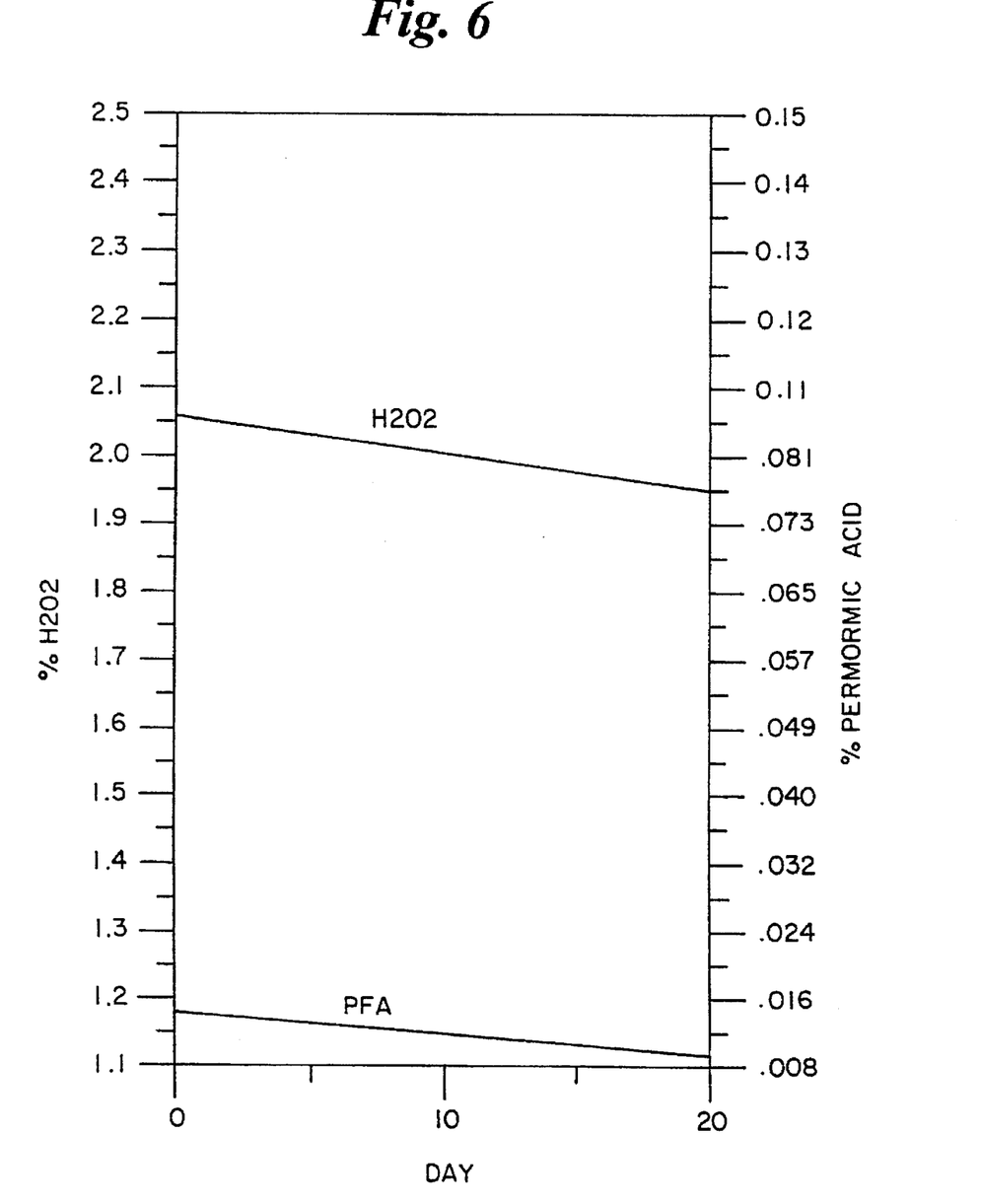
FIG. 6 illustrates the stability of hydrogen peroxide and performic acid in deionized water over time as measured in Example 3.

The results are also shown in FIGS. 4–6. FIG. 4 illustrates the concentration of performic acid in hard and deionized water over time. FIG. 5 illustrates the concentration of hydrogen peroxide in hard and deionized water over time. FIG. 6 illustrates the stability of hydrogen peroxide and performic acid in deionized water over time.

TABLE 3

| FORMULA # | DATE | FORMULATION EF, g | U/P, g | 50% H2O2 | WATER TYPE DI, g | TAP, g | HARD, g | TITRATION #1 DATE | % H2O2 | % PFA |
|---|---|---|---|---|---|---|---|---|---|---|
| 599-56-1 | 10/7/93 | 0.44 | 1.2 | | 20 | | | 10/7/93 | 2.09 | 0.0089 |
| 599-56-3 | 10/8/93 | 0.44 | 1.2 | | 20 | | | 10/8/93 | 2.11 | 0.0073 |
| 599-56-4 | 10/11/93 | 0.44 | 1.2 | | 20 | | | 10/11/93 | 2.08 | 0.0065 |
| 599-56-5 | 10/11/93 | 0.44 | 1.2 | | 20 | | | 10/11/93 | 2.08 | 0.0154 |
| 599-56-6 | 10/12/93 | 0.44 | 1.2 | | 20 | | | 10/12/93 | 1.91 | 0.0113 |
| 599-56-7 | 10/15/93 | 0.44 | 1.2 | | 20 | | | 10/15/93 | 2.08 | 0.0154 |
| 599-57-11 | 10/8/93 | 0.88 | 1.2 | | 20 | | | 10/8/93 | 2.11 | 0.0105 |
| 599-57-12 | 10/8/93 | 0.44 | 1.2 | | 20 | | | 10/8/93 | 3.83 | 0.0089 |
| 599-64-13-H | 10/25/93 | 0.44 | 1.2 | | | | 20 500PPPM Ca | 10/26/93 | 2.3 | 0.0211 |
| 599-64-14-H | 10/25/93 | 0.52 | 1.2 | | | | 20 500PPM Ca | 10/26/93 | 2.11 | 0.0130 |
| 599-65-15-T | 10/26/93 | 0.44 | 1.2 | | | 20 | | 10/26/93 | 2.06 | 0.0122 |
| 599-65-16-T | 10/26/93 | 0.44 | 1.2 | | | 20 | | 10/26/93 | 2.07 | 0.0105 |
| 599-65-17-T | 10/26/93 | 0.88 | 2.4 | | | 20 | | 10/26/93 | 2.86 | 0.0105 |
| 599-65-18-T | 10/26/93 | 0.88 | 2.4 | | | 20 | | 10/26/93 | 3.9 | 0.0178 |
| 599-65-19-T | 10/26/93 | 0.22 | 1.2 | | | 20 | | 10/26/93 | 2.08 | 0.0049 |
| 599-65-20-T | 10/26/93 | 0.22 | 1.2 | | | 20 | | 10/27/93 | 2.06 | 0.0162 |
| 599-66-13 | 10/29/93 | 0.22 | 0.6 | | 20 | | | 10/29/93 | 1.08 | 0.0357 |
| 599-66-14 | 10/29/93 | 0.22 | 0.6 | | 20 | | | 10/29/93 | 1.07 | 0.0008 |
| 599-66-15 | 10/29/93 | 0.22 | 0.6 | | 20 | | | 10/29/93 | 1.08 | 0.0081 |
| 599-66-16 | 10/29/93 | 0.22 | 0.6 | | 20 | | | 10/29/93 | 1.09 | 0.0041 |
| 599-80-1 | 11/18/93 | 0.44 | 1.2 | | 20 | | | 11/19/93 | 2.06 | 0.0113 |
| 599-80-2 | 11/18/93 | 0.44 | 1.2 | | 20 | | | 11/19/93 | 2.08 | 0.0122 |
| 599-80-3 | 11/18/93 | 0.44 | 1.2 | | 20 | | | 11/19/93 | 2.07 | 0.0105 |
| 599-80-4 | 11/18/93 | 0.44 | 1.2 | | 20 | | | 11/19/93 | 2.08 | 0.0081 |
| 599-80-5 | 11/18/93 | 0.44 | 1.2 | | | | 20 500PPM | | | |
| 599-80-6 | 11/18/93 | 0.44 | 1.2 | | | | 20 500PPM | 11/19/93 | 2.02 | 0.0251 |
| 599-80-7 | 11/18/93 | 0.44 | 1.2 | | | | 20 500PPM | 11/19/93 | 2.09 | 0.0130 |
| 599-80-8 | 11/18/93 | 0.44 | 1.2 | | | | 20 500PPM | 11/19/93 | 2.07 | 0.0154 |
| 599-80-9 | 11/18/93 | 0.44 | 1.2 | | | | 20 1000PPM | 11/19/93 | 2.07 | 0.0113 |
| 599-80-10 | 11/18/93 | 0.44 | 1.2 | | | | 20 1000PPM | 11/19/93 | 1.95 | 0.0113 |
| 599-81-11-Ca | 11/19/93 | 0.44 | 1.2 | | | | 20 500PM CaCl1 | 11/22/93 | 2.05 | 0.0138 |
| 599-81-42-Ca | 11/19/93 | 0.44 | 1.2 | | | | 20 500PPM CaCl2 | 11/22/93 | 2.06 | 0.0186 |
| 599-81-13-Bi | 11/19/93 | 0.44 | 1.2 | | | | 20 .22 g/L BICARB | 11/22/93 | 2.06 | 0.0097 |
| 599-81-14-Bi | 11/19/93 | 0.44 | 1.2 | | | | .22 g/L BICARB | 11/22/93 | 2.02 | 0.0122 |
| 599-81-15-Bc | 11/19/93 | 0.44 | 1.2 | | | | .22 g/L BICARB | 11/22/93 | 2.06 | 0.0178 |
| 599-81-16-Bc | 11/19/93 | 0.44 | 1.2 | | | | .22 g/L BICARB | 11/22/93 | 2.05 | 0.0178 |
| 599-81-17 | 11/19/93 | 0.44 | 1.2 | 1 quart | | | | 11/22/93 | 2.11 | 0.0130 |
| 599-81-18 | 11/19/93 | 0.44 | 1.2 | 1 quart | | | | 11/22/93 | 2.14 | 1.2231 |
| 599-81-19 | 11/19/93 | 1.32 | 3.6 | 1 quart | | | | 11/22/93 | 5.28 | 0.0502 |
| 599-81-20 | 11/19/93 | 1.32 | 3.6 | 1 quart | | | | 11/22/93 | 5.26 | 0.0292 |
| 599-83-21 | 11/23/93 | 1.8 | 4.8 | | 20 g | | | 11/23/93 | 6.72 | 0.0340 |
| 599-83-22 | 11/23/93 | 1.8 | 4.8 | | 20 g | | | 11/23/93 | 6.67 | 0.0292 |
| 599-83-23 | 11/23/93 | 1.8 | 4.8 | | | | 20 500PPM | 11/23/93 | 5.88 | 0.0446 |
| 599-83-24 | 11/23/93 | 1.8 | 4.8 | | | | 20 500PPM | 11/23/93 | 6.75 | 0.0470 |
| 599-83-25 | 11/23/93 | 1.8 | 4.8 | | | | 20 1000PPM | 11/23/93 | 6.7 | 0.0446 |
| 599-83-26 | 11/23/93 | 1.8 | 4.8 | | | | 20 1000PPM | 11/23/93 | 6.79 | 0.0494 |
| 599-83-27 | 11/23/93 | 1.8 | 4.8 | | | | 20 1000PPM Ca | 11/23/93 | 6.72 | 0.0462 |
| 599-83-28 | 11/23/93 | 1.8 | 4.8 | | | | 20 1000PPM Ca | 11/23/93 | 6.73 | 0.0494 |
| 599-83-29 | 11/23/93 | 1.8 | 4.8 | | 20 g | | | 11/23/93 | 6.72 | 0.0429 |
| 599-83-30 | 11/23/93 | 0 | 4.8 | | 20 g | | | 11/23/93 | 6.9 | 0.0089 |
| 599-83-31 | 11/23/93 | 1.8 | 0 | | 20 g | | | 11/23/93 | 0.004 | 0.0032 |
| 534-28-1 | 2/15/94 | 0.44 | 1.2 | | 20 g | | | 2/15/94 | mixing time and temperature | |
| 534-29-1 | 2/15/94 | 0.44 | | 0.8 | 18.76 | | | 2/17/94 | 2.12 | 0.0073 |
| 534-29-1T | 2/15/94 | 0.44 | | 0.8 | 18.76 | | | 2/17/94 | 2.12 | 0.0073 |
| 534-29-2 | 2/15/94 | 0.88 | | 0.8 | 18.32 | | | 2/17/94 | 2.25 | 0.00275 |
| 534-29-2T | 2/15/94 | 0.88 | | 0.8 | 18.32 | | | 2/17/94 | 2.25 | 0.0275 |
| 534-29-3 | 2/15/94 | 0.44 | | 1.6 | 17.96 | | | 2/17/94 | 4.2 | 0.0219 |

TABLE 3-continued

| | | | | | | | | |
|---|---|---|---|---|---|---|---|---|
| 534-29-3T | 2/15/94 | 0.44 | 1.6 | 17.96 | | 2/17/94 | 4.2 | 0.0219 |
| 534-29-4 | 2/15/94 | 0.88 | 1.6 | 17.52 | | 2/17/94 | 4.32 | 0.0259 |
| 534-29-4T | 2/15/94 | 0.88 | 1.6 | 17.52 | | 2/17/94 | 4.32 | 0.0259 |
| 534-29-5 | 2/15/94 | 1.76 | 1.6 | 16.64 | | 2/17/94 | 4.5 | 0.0243 |
| 534-29-5T | 2/15/94 | 1.76 | 1.6 | 16.64 | | 2/17/94 | 4.5 | 0.0243 |
| 534-29-6 | 2/15/94 | 0.44 | 3.2 | 16.36 | | 2/17/94 | 8.26 | 0.0284 |
| 534-29-6T | 2/15/94 | 0.44 | 3.2 | 16.36 | | 2/17/94 | 8.26 | 0.0284 |
| 534-29-7 | 2/15/94 | 0.88 | 3.2 | 15.92 | | 2/17/94 | 8.35 | 0.0251 |
| 534-29-7T | 2/15/94 | 0.88 | 3.2 | 15.92 | | 2/17/94 | 8.35 | 0.0251 |
| 534-29-8 | 2/15/94 | 1.76 | 3.2 | 15.04 | | 2/17/94 | 8.64 | 0.0267 |
| 534-29-8T | 2/15/94 | 1.76 | 3.2 | 15.04 | | 2/17/94 | 8.64 | 0.0267 |
| 534-29-9 | 2/15/94 | 1.76 | 3.2 | 15.04 | | 2/17/94 | 8.6 | 0.0535 |
| 534-29-9T | 2/15/94 | 1.76 | 3.2 | 15.04 | | 2/17/94 | 8.6 | 0.0535 |
| 534-29-10 | 2/15/94 | 3.52 | 3.2 | 13.28 | | 2/17/94 | 9.63 | 0.0599 |
| 534-29-10T | 2/15/94 | 3.52 | 3.2 | 13.28 | | 2/17/94 | 9.63 | 0.0599 |
| 534-29-11 | 2/15/94 | 8 | 52 | 0 | | 2/17/94 | 44.9 | 0.2349 |
| 534-29-11T | 2/15/94 | 8 | 52 | 0 | | 2/17/94 | 44.9 | 0.2349 |
| 534-29-12 | 2/15/94 | 6 | 54 | 0 | | 2/17/94 | 46.8 | 0.5249 |
| 534-29-12T | 2/15/94 | 6 | 54 | 0 | | 2/17/94 | 46.8 | 0.5249 |
| 534-29-13 | 2/15/94 | 4 | 56 | 0 | | 2/17/94 | 46.1 | 0.2584 |
| 534-29-13T | 2/15/94 | 4 | 56 | 0 | | 2/17/94 | 46.1 | 0.2584 |
| 534-29-14 | 2/15/94 | 2 | 58 | 0 | | 2/17/94 | 49.8 | 0.1393 |
| 534-29-14T | 2/15/94 | 2 | 58 | 0 | | 2/17/94 | 49.8 | 0.1393 |
| 534-29-15 | 2/15/94 | 10 | 50 | 0 | | 2/17/94 | 45.6 | 0.4755 |
| 534-29-15T | 2/15/94 | 10 | 50 | 0 | | 2/17/94 | 45.6 | 0.4755 |
| 534-29-16 | 2/15/94 | 1.76 | 3.2 | 7.04 | 8 g 1000PPM | 2/17/94 | 8.48 | 0.0275 |
| 534-29-16T | 2/15/94 | 1.76 | 3.2 | 7.04 | 8 g 1000PPM | 2/17/94 | 8.48 | 0.0275 |
| 524-29-17 | 2/15/94 | 1.76 | 3.2 | 9.04 | 6 g 1000PPM | 2/17/94 | 8.61 | 0.0543 |
| 524-29-17T | 2/15/94 | 1.76 | 3.2 | 9.04 | 6 g 1000PPM | 2/17/94 | 8.61 | 0.0543 |
| 524-29-18 | 2/15/94 | 1.76 | 3.2 | 11.04 | 4 g 1000PPM | 2/17/94 | 8.52 | 0.0697 |
| 524-29-18T | 2/15/94 | 1.76 | 3.2 | 11.04 | 4 g 1000PPM | 2/17/94 | 8.52 | 0.0697 |
| 524-29-19 | 2/15/94 | 1.76 | 3.2 | 13.04 | 2 g 1000PPM | 2/17/94 | 8.58 | 0.0680 |
| 524-29-19T | 2/15/94 | 1.76 | 3.2 | 13.04 | 2 g 1000PPM | 2/17/94 | 8.58 | 0.0680 |
| 529-29-20 | 2/15/94 | 1.76 | 3.2 | 14.04 | 1 g 1000PPM | 2/17/94 | 8.57 | 0.0680 |
| 529-29-20T | 2/15/94 | 1.76 | 3.2 | 14.04 | 1 g 1000PPM | 2/17/94 | 8.57 | 0.0770 |
| 529-29-21 | 2/15/94 | 1.76 | 3.2 | 6.8 | 10 g 1000PPM | 2/17/94 | 6.98 | 0.0770 |
| 529-29-21T | 2/15/94 | 1.76 | 3.2 | 6.8 | 10 g 1000PPM | 2/17/94 | 6.98 | 0.0648 |
| 529-29-22 | 2/15/94 | 0 | 3.2 | 16.8 | | 2/17/94 | 8.14 | 0.0648 |
| 529-29-22T | 2/15/94 | 0 | 3.2 | 16.8 | | 2/17/94 | 8.14 | 0.0356 |
| 529-29-23 | 2/15/94 | 0.44 | 0.8 | 18.72 | .04 g COBRATEC 99 | 2/17/94 | 2.18 | 0.0356 |
| 529-29-23T | 2/15/94 | 0.44 | 0.8 | 18.72 | .04 g COBRATEC 99 | 2/17/94 | 2.18 | 0.0186 |
| 529-29-24 | 2/15/94 | 0.44 | 1.2 | 20 | | 2/17/94 | 2.09 | 0.0186 |
| 529-29-24T | 2/15/94 | 0.44 | 1.2 | 20 | | 2/17/94 | 2.09 | 0.0154 |
| 529-29-25 | 2/15/94 | 0.44 | 1.2 | 20 | | 2/17/94 | 2.09 | 0.0170 |
| 529-29-25T | 2/15/94 | 0.44 | 1.2 | 20 | | 2/17/94 | 2.09 | 0.0170 |
| 529-29-26 | 2/15/94 | 0 | 3.2 | 16.8 | | 2/17/94 | 8.66 | 0.0348 |
| 529-29-26T | 2/15/94 | 0 | 3.2 | 16.8 | | 2/17/94 | 8.66 | 0.348 |

| | TITRATION #2 | | | TITRATION #3 | | | TITRATION #4 | | |
|---|---|---|---|---|---|---|---|---|---|
| FORMULA # | DATE | % H2O2 | % PFA | DATE | % H2O2 | % PFA | DATE | % H2O2 | % PFA |
| 599-56-1 | 10/8/93 | 1.06 | 0.0154 | 10/11/93 | 2.07 | 0.0146 | 10/12/93 | 2.08 | 0.0162 |
| 599-56-3 | 10/11/93 | 2.09 | 0.0122 | 10/11/93 | 2.1 | 0.0122 | 10/12/93 | 2.1 | 0.0154 |
| 599-56-4 | 10/12/93 | 2.08 | 0.0138 | 10/14/93 | 2.07 | 0.0162 | 10/25/93 | 1.99 | 0.0041 |
| 599-56-5 | 10/12/93 | 2.07 | 0.0113 | 10/14/93 | 2.07 | 0.0138 | 10/15/93 | 2.06 | 0.0186 |
| 599-56-6 | 10/14/93 | 1.92 | 0.0130 | 10/25/93 | 1.86 | 0.0122 | 2/15/94 | 1.49 | 0.0105 |
| 599-56-7 | 10/25/93 | 2.04 | 0.0219 | 2/15/94 | 1.64 | 0.0146 | | | |
| 599-57-11 | 10/8/93 | 2.15 | 0.0122 | 10/12/93 | 2.08 | 0.0162 | 10/14/93 | 2.04 | 0.0130 |
| 599-57-12 | 10/8/93 | 3.84 | 0.0073 | 10/12/93 | 3.78 | 0.0122 | 10/14/93 | 3.75 | 0.0105 |
| 599-64-13-H | 10/26/93 | 2.09 | 0.0518 | 10/26/93 | 2.03 | 0.0154 | 10/26/93 | 2.04 | 0.0138 |
| 599-64-14-H | 11/2/93 | 2.03 | 0.0186 | 11/18/93 | 1.84 | 0.0194 | 2/15/94 | 1.41 | 0.0535 |
| 599-65-15-T | 10/27/93 | 2.03 | 0.0122 | 11/2/93 | 1.99 | 0.0049 | 11/18/93 | 1.85 | 0.0032 |
| 599-65-16-T | 11/2/93 | 1.99 | 0.0049 | 11/18/93 | 1.85 | 0.0073 | 2/15/94 | 1.42 | 0.0186 |
| 599-65-17-T | 10/27/93 | 3.81 | 0.0259 | 11/2/93 | 3.6 | 0.0113 | 11/18/93 | 3.13 | 0.0146 |
| 599-65-18-T | 11/2/93 | 3.63 | 0.0170 | 11/18/93 | 31.5 | 0.0122 | 2/15/94 | 2.25 | 0.0105 |
| 599-65-19-T | 10/26/93 | 2.06 | 0.0097 | 2/15/94 | 1.72 | 0.0211 | | | |
| 599-65-20-T | 2/15/94 | 1.67 | 0.0041 | | | | | | |
| 599-66-13 | 11/2/93 | 1.08 | 0.0081 | 2/15/94 | 0.93 | 0.0348 | | | |
| 599-66-14 | 11/2/93 | 1.08 | 0.0081 | 2/15/94 | 0.94 | 0.0235 | | | |
| 599-66-15 | 11/2/93 | 1.09 | 0.0041 | 2/15/94 | 0.96 | 0.0203 | | | |
| 599-66-16 | 11/2/93 | 1.09 | 0.0057 | 2/15/94 | 0.94 | 0.0251 | | | |
| 599-80-1 | 11/22/93 | 2.04 | 0.0073 | 2/15/94 | 1.59 | 0.0105 | | | |
| 599-80-2 | 11/22/93 | 2.07 | 0.0162 | 2/15/94 | 1.65 | 0.0113 | | | |
| 599-80-3 | 11/22/93 | 2.05 | 0.0097 | 2/15/94 | 1.64 | 0.0243 | | | |
| 599-80-4 | 11/22/93 | 2.06 | 0.0154 | 2/15/94 | 1.61 | 0.0170 | | | |
| 599-80-6 | 11/22/93 | 1.99 | 0.0146 | 2/15/94 | 1.56 | 0.0834 | | | |
| 599-80-7 | 11/22/93 | 2.06 | 0.1539 | 2/15/94 | 1.56 | | | | |
| 599-80-8 | 11/22/93 | 2.04 | 0.0170 | 2/15/94 | 1.54 | 0.0656 | | | |

TABLE 3-continued

| | | | | | | | | | |
|---|---|---|---|---|---|---|---|---|---|
| 599-80-9 | 11/22/93 | 2.03 | 0.0154 | 2/15/94 | 1.4 | 0.0810 | | | |
| 599-80-10 | 11/22/93 | 1.94 | 0.0178 | 2/14/94 | 1.39 | 0.0640 | | | |
| 599-81-11-Ca | 2/14/94 | 1.6 | 0.0397 | | | | | | |
| 599-81-42-Ca | 2/14/94 | 1.58 | 0.0413 | | | | | | |
| 599-81-13-Bi | 2/14/94 | 1.64 | 0.0130 | | | | | | |
| 599-81-14-Bi | 2/14/94 | 1.66 | 0.0130 | | | | | | |
| 599-81-15-Bc | 2/14/94 | 106 | 0.0664 | | | | | | |
| 599-81-17 | 2/14/94 | 1.69 | 0.0105 | | | | | | |
| 599-81-18 | 2/14/93 | 1.5 | 0.0243 | | | | | | |
| 599-81-19 | 2/14/93 | 3.13 | 0.1134 | 2/15/94 | 3.15 | 0.0284 | | | |
| 599-81-20 | 2/14/93 | 3.22 | 0.0486 | 2/15/94 | 3.2 | 0.0275 | 2/15/94 | 3.16 | 0.0308 |
| 599-83-21 | 12/3/93 | 5.58 | 0.0308 | 2/14/94 | 3.79 | 0.0365 | | | |
| 599-83-22 | 12/3/93 | 5.38 | 0.0373 | 2/14/94 | 3.66 | 0.0340 | | | |
| 599-83-23 | 12/3/93 | 4.97 | 0.0624 | 2/14/94 | 3.26 | 0.0421 | | | |
| 599-83-24 | 12/3/93 | 5.49 | 0.0632 | 2/14/94 | 3.69 | 0.0365 | | | |
| 599-83-25 | 12/3/93 | | 0.0923 | 2/14/94 | 3.39 | 0.0421 | | | |
| 599-83-26 | 12/3/93 | 5.41 | 0.0899 | 2/14/94 | 3.51 | 0.0713 | | | |
| 599-83-27 | 12/3/93 | 5.63 | 0.0729 | 2/14/94 | 3.74 | 0.0421 | | | |
| 599-83-28 | 12/14/93 | 3.74 | 0.0365 | | | | | | |
| 599-83-29 | 12/14/93 | 3.76 | 0.0348 | | | | | | |

| | TITRATION #5 | | | TITRATION #6 | | | TITRATION #7 | | |
|---|---|---|---|---|---|---|---|---|---|
| FORMULA # | DATE | % H2O2 | % PFA | DATE | % H2O2 | % PFA | DATE | % H2O2 | % PFA |
| 599-56-1 | 10/14/93 | 2.04 | 0.0138 | 10/15/93 | 2.02 | 0.0154 | 10/25/93 | 1.96 | 0.0073 |
| 599-56-3 | 10/14/93 | 2.08 | 0.0138 | 10/25/93 | 1.99 | 0.0081 | 10/27/93 | 1.98 | 0.0146 |
| 599-56-4 | 10/27/93 | 2 | 0.0073 | 2/15/94 | 1.52 | 0.0186 | | | |
| 599-56-5 | 10/25/93 | 1.98 | 0.0275 | 10/25/93 | 1.97 | 0.0267 | 10/27/93 | 1.98 | 0.0454 |
| 599-57-11 | 10/25/93 | 1.86 | 0.0130 | 2/15/94 | 0.95 | 0.0235 | | | |
| 599-57-12 | 10/25/93 | 3.59 | 0.0113 | 2/15/94 | 1.36 | 0.0194 | | | |
| 599-64-23-H | 10/27/93 | 2.04 | 0.0178 | 11/2/93 | 2 | 0.0178 | 11/18/93 | 1.82 | 0.0203 |
| 599-65-15-T | 2/15/94 | 1.43 | 0.0365 | | | | | | |
| 599-65-17-T | 2/15/94 | 2.24 | 0.0089 | | | | | | |

| | TITRATION #8 | | | TITRATION #9 | | | TITRATION #10 | | |
|---|---|---|---|---|---|---|---|---|---|
| FORMULA # | DATE | % H2O2 | % PFA | DATE | % H2O2 | % PFA | DATE | % H2O2 | % PFA |
| 599-56-1 | 10/27/93 | 1.94 | 0.0081 | 11/2/93 | 1.89 | 0.0146 | 11/8/93 | 1.78 | 0.0065 |
| 599-56-3 | 2/15/94 | 1.44 | 0.0316 | | | | | | |
| 599-56-5 | 10/29/93 | 1.95 | 0.0356 | 11/2/93 | 1.92 | 0.0267 | 11/18/93 | 1.81 | 0.0292 |
| 599-64-13-H | 2/15/94 | 1.38 | 0.0332 | | | | | | |

| | TITRATION #11 | | |
|---|---|---|---|
| FORMULA # | DATE | % H2O2 | % PFA |
| 599-56-5 | 2/15/94 | 1.4 | 0.0243 |

While the invention has been described in detail and with reference to specific embodiments thereof, it will be apparent to one of ordinary skill in the art that various changes and modifications can be made therein without departing from the spirit and scope thereof.

What is claimed is:

1. A premix for making an anti-microbial composition comprising an ester of formic acid, an oxidizer, performic acid, and water, the premix comprising:
   a first part comprising said ester of formic acid; and
   a second part comprising said oxidizer.

2. A premix according to claim 1, wherein said ester of formic acid is selected from the group consisting of ethyl formate, methyl formate, propyl formate, and mixtures thereof.

3. A premix according to claim 2, wherein said ester of formic acid is ethyl formate.

4. A premix according to claim 1, wherein said oxidizer is hydrogen peroxide.

5. A premix according to claim 2, wherein said oxidizer is hydrogen peroxide.

6. A premix according to claim 3, wherein said oxidizer is hydrogen peroxide.

7. A premix according to claim 1, wherein at least one of said first and second components is in a dry form.

8. A premix according to claim 2, wherein at least one of said first and second components is in dry form.

9. A premix according to claim 1, wherein said at least one of said first and second parts is in a concentrated liquid form.

10. A premix according to claim 2, wherein said at least one of said first and second parts is in a concentrated liquid form.

11. A premix according to claim 1, wherein at least one of said first and second parts further comprises an additive selected from the group consisting of corrosion inhibitors, stabilizers, and mixtures thereof.

12. A premix according to claim 2, wherein at least one of said first and second parts further comprises an additive selected from the group consisting of corrosion inhibitors, stabilizers, and mixtures thereof.

13. A premix according to claim 6, wherein at least one of said first and second parts further comprises an additive selected from the group consisting of corrosion inhibitors, stabilizers, and mixtures thereof.

14. A premix according to claim 11, wherein said additive comprises:

a) about 20% to about 45% by weight mono sodium salt of phosphoric acid, mono(2-ethyl hexyl) ester;

b) about 20% to about 30% by weight pyrophosphonic acid, bis(2-ethyl hexyl) esters, sodium salts;

c) about 10% to about 25% by weight polyphosphonic acids, 2-ethyl hexyl esters, sodium salts;

d) about 20% to 25% by weight water;

e) less than 10% by weight phosphoric acid, bis(2-ethyl hexyl) esters, sodium salt;

f) less than 3% by weight 2-ethyl hexanol; and g) less than 5% by weight phosphoric acid, sodium salts, mono and di.

15. A premix according to claim 12, wherein said additive comprises:

a) about 20% to about 45% by weight mono sodium salt of phosphoric acid, mono(2-ethyl hexyl) ester;

b) about 20% to about 30% by weight pyrophosphonic acid, bis(2-ethyl hexyl) esters, sodium salts;

c) about 10% to about 25% by weight polyphosphonic acids, 2-ethyl hexyl esters, sodium salts;

d) about 20% to 25% by weight water;

e) less than 10% by weight phosphoric acid, bis(2-ethyl hexyl) esters, sodium salt;

f) less than 3% by weight 2-ethyl hexanol; and g) less than 5% by weight phosphoric acid, sodium salts, mono and di.

16. A premix according to claim 13, wherein said additive comprises:

a) about 20% to about 45% by weight mono sodium salt of phosphoric acid, mono(2-ethyl hexyl) ester;

b) about 20% to about 30% by weight pyrophosphonic acid, bis(2-ethyl hexyl) esters, sodium salts;

c) about 10% to about 25% by weight polyphosphonic acids, 2-ethyl hexyl esters, sodium salts;

d) about 20% to 25% by weight water;

e) less than 10% by weight phosphoric acid, bis(2-ethyl hexyl) esters, sodium salt;

f) less than 3% by weight 2-ethyl hexanol; and g) less than 5% by weight phosphoric acid, sodium salts, mono and di.

17. A premix according to claim 11, wherein said additive comprises 1,2,3-Benzotriazole.

18. A premix according to claim 12, wherein said additive comprises 1,2,3-Benzotriazole.

19. A premix according to claim 13, wherein said additive comprises 1,2,3-Benzotriazole.

20. A premix according to claim 1, wherein said first part, said second part, or said first and second part combined, contain water, whereby no water is required to be added to form said anti-microbial composition.

21. A premix according to claim 2, wherein said first part, said second part, or said first and second part combined, contain water, whereby no water is required to be added to form said anti-microbial composition.

22. A premix according to claim 6, wherein said first part, said second part, or said first and second part combined, contain water, whereby no water is required to be added to form said anti-microbial composition.

23. A premix according to claim 11, wherein said first part, said second part, or said first and second part combined, contain water, whereby no water is required to be added to form said anti-microbial composition.

24. A method of making an anti-microbial composition having improved anti-corrosive properties comprising an ester of formic acid, an oxidizer, performic acid, and water, the method comprising:

combining said first part and said second part of said premix of claim 1 with water.

25. A method according to claim 24, wherein a sufficient amount of water is added to provide an anti-microbial composition having about 0.01 to about 10 wt. % of said ester of formic acid, about 0.01 to about 10 wt. % of said oxidizer, about 0.001 to about 5 wt. % of performic acid, and up to about 99.98 wt. % water.

26. A method of making an anti-microbial composition having improved anti-corrosive properties comprising an ester of formic acid, an oxidizer, performic acid, and water, the method comprising:

combining said first part and said second part of said premix of claim 2 with water.

27. A method according to claim 26, wherein a sufficient amount of water is added to provide an anti-microbial composition having about 0.01 to about 10 wt. % of said ester of formic acid, about 0.01 to about 10 wt. % of said oxidizer, about 0.001 to about 5 wt. % of performic acid, and up to about 99.98 wt. % water.

28. A method of making an anti-microbial composition having improved anti-corrosive properties comprising an ester of formic acid, an oxidizer, performic acid, and water, the method comprising:

combining said first part and said second part of said premix of claim 6 with water.

29. A method according to claim 28, wherein a sufficient amount of water is added to provide an anti-microbial composition having about 0.01 to about 10 wt. % of said ester of formic acid, about 0.01 to about 10 wt. % of said oxidizer, about 0.001 to about 5 wt.% of performic acid, and up to about 99.98 wt. % water.

30. A method of making an anti-microbial composition having improved anti-corrosive properties comprising an ester of formic acid, an oxidizer, performic acid, and water, the method comprising:

combining said first part and said second part of said premix of claim 11 with water.

31. A method according to claim 30, wherein a sufficient amount of water is added to provide an anti-microbial composition having about 0.01 to about 10 wt. % of said ester of formic acid, about 0.01 to about 10 wt. % of said oxidizer, about 0.001 to about 5 wt. % of performic acid, and up to about 99.98 wt. % water.

32. A method of making an anti-microbial composition having improved anti-corrosive properties comprising an ester of formic acid, an oxidizer, performic acid, and water, the method comprising:

combining said ester of formic acid, said oxidizer and water.

33. A method according to claim 32, wherein a sufficient amount of water is added to provide an anti-microbial composition having about 0.01 to about 10 wt. % of said ester of formic acid, about 0.01 to about 10 wt. % of said oxidizer, about 0.001 to about 5 wt. % of performic acid, and up to about 99.98 wt. % water.

34. A method according to claim 33, further comprising adding an additive selected from the group consisting of corrosion inhibitors, stabilizers, and mixtures thereof.

* * * * *

UNITED STATES PATENT AND TRADEMARK OFFICE
CERTIFICATE OF CORRECTION

PATENT NO. : 5,635,195
DATED : June 3, 1997
INVENTOR(S) : Hall, et al.

It is certified that error appears in the above-indentified patent and that said Letters Patent is hereby corrected as shown below:

Column 3, line 54, delete "Victawet" and substitute --Victawet$^{TM}$-- therefor.

Column 4, line 41, delete "Here" and substitute --were-- therefor.

Column 8, Table 3, delete "0.0357" in the last column (% PFA), row beginning "599-66-13" and substitute --0.0057-- therefor.

Column 8, Table 3, delete "0.00275" in the last column (% PFA), row beginning "534-29-2" and substitute --0.0275-- therefor.

Column 9, Table 3-continued, delete "1.06" in the third column (% H2O2), row beginning "599-56-1" and substitute --2.06-- therefor.

Column 12, Table 3-continued, delete "2,02" in the second column (Titration #6, %h2O2), row beginning "599-56-1" and substitute --2.02-- therefor.

UNITED STATES PATENT AND TRADEMARK OFFICE
CERTIFICATE OF CORRECTION

PATENT NO. : 5,635,195
DATED : June 3, 1997
INVENTOR(S) : Hall, et al.

It is certified that error appears in the above-indentified patent and that said Letters Patent is hereby corrected as shown below:

Column 11, Table 3-continued, delete "599-64-23-H" in the first column (Formula #), and substitute --599-64-13-H-- therefor.

Column 11, Table 3-continued, delete "0.0365" in the third column (Titration #5, % PFA), row beginning "599-65-15-T" and substitute --0.0065-- therefor.

Signed and Sealed this

Twenty-first Day of October 1997

Attest:

BRUCE LEHMAN

Attesting Officer           Commissioner of Patents and Trademarks